United States Patent [19]

Wang et al.

[11] Patent Number: 6,093,866
[45] Date of Patent: *Jul. 25, 2000

[54] ALKYLATION CATALYST AND THE APPLICATION THEREOF

[75] Inventors: Qingxia Wang; Shurong Zhang; Guangyu Cai; Feng Li; Longya Xu, all of Liaoning; Zuxian Huang, Liaonig; Yuying Li, Liaoning, all of China

[73] Assignees: China Petro-Chemical Corporation, Beijing; Dalian Institute of Chemical Physics, Chinese Academy of Sciences, Liaoning; Fushun Petrochemical Company of Sinopec, Fushun, all of China

[*] Notice: This patent is subject to a terminal disclaimer.

[21] Appl. No.: 08/880,741

[22] Filed: Jun. 23, 1997

[30] Foreign Application Priority Data

Jun. 24, 1996 [CN] China ..................................... 96106561
[51] Int. Cl.⁷ ..................................................... C07C 2/68
[52] U.S. Cl. ............................. 585/467; 585/446; 502/64; 502/65; 502/67; 502/71; 502/73
[58] Field of Search .................................. 502/64, 65, 67, 502/71, 73; 585/446, 467

[56] References Cited

U.S. PATENT DOCUMENTS

| 3,702,886 | 11/1972 | Argauer | 423/328 |
| 4,108,881 | 8/1978 | Rollmann et al. | 260/448 |
| 4,229,424 | 10/1980 | Kokotailo | 423/328 |
| 4,372,839 | 2/1983 | Oleck et al. | 208/59 |

FOREIGN PATENT DOCUMENTS

| 1020041 | 3/1993 | China . |
| 1022404 | 10/1993 | China . |
| 1137022 | 12/1996 | China . |

*Primary Examiner*—Tom Dunn
*Attorney, Agent, or Firm*—Burns, Doane, Swecker & Mathis LLP

[57] ABSTRACT

An alkylation catalyst comprises from 50 to 70 wt % of hydrogen type ZSM-5/ZSM-11 co-crystaline zeolite containing rare earth element and the rest amount of porous inorganic oxide matrix material. The zeolite has particular chemical composition and X-ray diffraction lines. This catalyst has higher activity, selectivity and stability in alkylation process than that of the prior art. With this catalyst the process for preparing ethyl benzene by alkylation of benzene with ethylene has higher ethylene conversion and ethyl benzene selectivity.

8 Claims, No Drawings

ALKYLATION CATALYST AND THE APPLICATION THEREOF

FIELD OF THE INVENTION

The present invention relates to an alkylation catalyst containing zeolite and the application thereof. More particularly, this invention relates to an alkylation catalyst containing aluminosilicate zeolite and the application thereof in a process for preparing ethyl benzene by alkylation of benzene with ethylene.

BACKGROUND OF THE INVENTION

CN Pat. Appl. No. 94113403.2 (Filing Date: Dec. 30, 1994) teaches a synthesis of ZSM-5 and ZSM-11 co-crystalline zeolite containing rare earth element, which is different from the zeolite described in U.S. Pat. No. 4,229,424. This zeolite has a weight ratio of ZSM-5 crystalline structure portion to ZSM-11 crystalline structure portion in the range of 0.05 to 20; and in its originally synthesized anhydrous state a chemical composition formula in terms of mole ratios of oxides as follows:

$$XNa_2O \cdot YRE_2O_3 \cdot Al_2O_3 \cdot ZSiO_2$$

wherein X is within the range of 0.1 to 1.0, Y is within the range of 0.1 to 1.0, and Z is within the range of 20 to 300; and its adsorption capacities range from 9 to 11 wt %, from 3 to 4 wt % and from 4 to 8 wt % respectively for n-hexane, cyclohexane and water, and provides an X-ray diffraction pattern comprising the following X-ray diffraction lines and assigned relative intensities;

| d(A) | 100 I/I$_o$ |
|---|---|
| 11.2 ± 0.2 | M |
| 10.1 ± 0.2 | M |
| 6.05 ± 0.14 | W |
| 4.40 ± 0.08 | W |
| 3.86 ± 0.07 | VS |
| 3.72 ± 0.07 | S |
| 3.65 ± 0.07 | W–M |
| 2.01 ± 0.02 | W |

VS = very strong (100–60); S = strong (60–40); M = medium (40–20); W = weak (<20)

The processes for preparing ethyl benzene by alkylation of benzene with ethylene can be generally divided into three kinds, namely liquid-phase AlCl$_3$ process, BF$_3$ process and vapor-phase silicate zeolite process. The catalyst used in vapor-phase silicate zeolite process is zeolite catalyst, which normally is Pentasil type zeolite or ZSM series zeolite catalyst. For example, U.S. Pat. No. 4,107,224 discloses a process for manufacturing ethyl benzene from benzene and dilute ethylene raw materials, in which the reaction conditions include a temperature ranging from 250 to 600° C., a pressure ranging from 0.1 to 100 atmospheres, a feedstock weight hourly space velocity ranging from 0.1 to 100 hr$^{-1}$, a molar ratio of benzene to ethylene ranging from 1 to 30 and a catalyst containing a ZSM-5, -11, -12, -35 or -38 zeolite. Like the previous techniques in the prior art this process has comparatively strict requirement for contents of impurities in the raw materials. The raw material gas must contain no such acidic gases as H$_2$S and CO$_2$, water and hydrocarbons of more than two carbon atoms.

In order to overcome the above drawback, CN 1051166A and CN 1031072A disclose respectively the processes for preparing ethyl benzene from un-pre-refined ethylene raw material and the catalyst used therein. In the processes the ethylene raw material is only required containing no free water, H$_2$S content less than 6000 mg/m$^3$ and C$_3$$^=$ and C$_4$$^=$ contents less than 2 vol %. The catalyst used is a Pentasil type zeolite catalyst comprising from 0.3 to 6 wt % of a mixture of rare earth elements or from 0.2 to 3 wt % of lanthanum, from 0.05 to 0.2 wt % of sulfur, from 30 to 70 wt % of zeolite and from 70 to 30 wt % of Al$_2$O$_3$ having SiO$_2$/Al$_2$O$_3$ ratio in the range of 40 to 100. Although the process for preparing ethyl benzene with this catalyst has solved the problem of the requirement for pre-refined raw material in the previous processes, the ethylene conversion is only in the range of 72.97 to 98.51 wt %, the ethyl benzene selectivity is only in the range of 76.84 to 89.89 wt %, the alkylation selectivity (as total amount of ethyl benzene and diethyl benzene produced) is also merely in the range of 98 to 99%. The single operation cycle for a catalyst is merely between 40 to 60 days, it means that the activity and stability of the catalyst are not sufficiently high.

SUMMARY OF THE INVENTION

An object of the present invention is to provide an alkylation catalyst having high activity and high selectivity in order to overcome the drawback of lower activity and stability of the catalyst in the prior art. Another object of the present invention is to provide a process for preparing ethyl benzene by alkylation of benzene with ethylene over the said catalyst, which has high conversion and high selectivity, in order to overcome the drawback of relatively low ethylene conversion and ethyl benzene selectivity in the process of the prior art. Other objects of the present invention can be known from the following description, including examples.

The present invention relates to an alkylation catalyst comprising from 50 to 70 wt % of hydrogen type ZSM-5/ZSM-11 co-crystalline zeolite containing rare earth element based on the weight of the catalyst, and the balance amount of porous inorganic oxide matrix material based on the weight of the catalyst. The said zeolite has a weight ratio of ZSM-5 crystalline structure portion to ZSM-11 crystalline structure portion within the range of 0.25 to 2.5 and in its originally synthesized anhydrous statea chemical composition formula in terms of mole ratios of oxides as follows:

$$XNa_2O \cdot YRE_2O_3 \cdot Al_2O \cdot ZSiO_2$$

wherein X is within the range of 0.1 to 1.0, Y is within the range of 0.1 to 1.0 and Z is within the range of 20 to 100, and provides an X-ray diffraction pattern comprising the X-ray diffraction lines and assigned relative intensities shown in Table 1.

TABLE 1

| d(A) | 100 I/I$_o$ |
|---|---|
| 11.2 ± 0.2 | M |
| 10.1 ± 0.2 | M |
| 6.05 ± 0.14 | W |
| 4.40 ± 0.08 | W |
| 3.86 ± 0.07 | VS |
| 3.72 ± 0.07 | S |
| 3.65 ± 0.07 | W–M |
| 2.01 ± 0.02 | W |

VS = strong (100–60); S = strong (60–40); M = medium (40–20); W = weak (<20)

The present invention also relates to a process for preparing ethyl benzene by alkylation of benzene with ethylene, comprising contacting benzene and ethylene with a zeolite-containing catalyst under conditions enabling the alkylation reaction to be performed, and separating the product from side products and unreacted reactants. The said catalyst comprises from 50 to 70 wt % of ZSM-5/ZSM-11 co-crystalline zeolite containing rare earth element based on the weight of the catalyst, and the balance amount of porous inorganic oxide matrix material based on the weight of the catalyst. The said zeolite has a weight ratio of ZSM-5 crystalline structure portion to ZSM-11 crystalline structure portion within the range of 0.25 to 2.5 and in its originally synthesized anhydrous state a chemical composition formula in terms of mole ratios of oxides as follows:

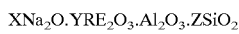

$XNa_2O.YRE_2O_3.Al_2O_3.ZSiO_2$ wherein X is within the range of 0.1 to 1.0, Y is within the range of 0.01 to 1.0 and Z is within the range of 20 to 100, and provides an X-ray diffraction pattern comprising the X-ray diffraction lines and assigned relative intensities as shown in Table 1.

DETAILED DESCRIPTION OF THE INVENTION

The catalyst provided in accordance with the present invention comprises from 50 to 70 wt % of ZSM-5/ZSM-11 co-crystalline zeolite containing rare earth element and from 50 to 30 wt % of porous inorganic oxide matrix material, based on the weight of the catalyst. The rare earth element is present in the catalyst in an amount ranging preferably from 0.5 to 5 wt % (calculated as element) based on the weight of the catalyst. The said rare earth element may be lanthanum or a mixture of rare earth elements.

The said porous inorganic oxide matrix material may be a common support or/and binder used in the art, such as alumina, silica, silica-alumina, silica-zirconia, preferably alumina.

The sodium oxide present in the catalyst is preferably in an amount less than 0.05 wt %, based on the weight of the catalyst.

The catalyst provided by the present invention may be employed as an alkylation catalyst not only for reaction of benzene with ethylene, but also for other reactions such as the reaction of benzene with an alkene of $C_3$ to $C_{12}$.

The catalyst provided by the present invention may be prepared by a method which comprises:

(1) mixing a pre-determined amount of the ZSM-5/ZSM-11 co-crystalline zeolite containing rare earth element with a determined amount of a porous inorganic oxide matrix material precursor, shaping, drying at the temperature between 110 and 120° C., and calcining in an inert gas stream or air at the temperature ranging from 500 to 550° C. for 5 to 10 hours;

(2) replacing the original cations of the product obtained in step (1) with ammonium ions by ion-exchanging in an aqueous solution of ammonium salt or a mixture of aqueous solutions of ammonium salt and aqua ammonia, separating the solid, washing it until the wash filtrate has no anion from the salt, drying, and calcining in the inert gas stream or air at a temperature ranging from 500 to 550° C. for 3 to 8 hours;

(3) hot-treating the product obtained in step (2) in a 100% steam atmosphere at a temperature ranging from 500 to 560° C. for 3 to 10 hours.

The said ZSM-5/ZSM-11 co-crystalline zeolite containing rare earth element used therein is prepared in accordance with the method described in Chinese Pat. Appl. No. 94113403.2, which comprises mixing, under vigorous stirring, a homogeneous mixture I containing sodium silicate, a diamine of 2 to 8 carbon atoms and water, with a mixture II containing a source of aluminum, inorganic acid, salt of rare earth element and water to form gel; crystallizing the gel under stirring at the temperature of 100 to 200° C. for 0.5 to 4 days; cooling it to the room temperature rapidly, washing the crystalline with deionized water until the pH of the wash filtrate reaching a value ranging from 8 to 9 and drying to give the zeolite. The said raw material has a molar ratio of $Na_2O$ to $Al_2O_3$ ranging from 7 to 12; a molar ratio of $RE_2O_3$ to $Al_2O_3$ ranging from 0.1 to 1.0, a molar ratio of $SiO_2$ to $Al_2O_3$ ranging from 30 to 200, a molar ratio of amine to $SiO_2$ ranging from 0.1 to 0.5 and a molar ratio of $H_2O$ to $SiO_2$ ranging from 20 to 100. The said diamine used in the synthesis is any one chosen from primary diamines of 2 to 8 carbon atoms or a mixture of any two of these primary diamines. The said source of aluminum is chosen from $AlCl_3$, $AlBr_3$, $Al(NO_3)_3$, $Al_2(SO_4)_3$ and $AlPO_4$. The said inorganic acid is chosen from $H_2SO_4$, HCl, $HNO_3$ and $H_3PO_4$.

The said porous inorganic oxide matrix material precursor used in preparing the catalyst is precursors commonly used in the art, such as hydrate alumina, silica hydrosol, silica-alumina hydrosol, a mixture of silica hydrosol and zirconium hydroxide, and the like, and said hydrate alumina is preferred. The said shaping method is a conventional shaping method used in the art such as extrusion, pelletization and drop-shaping method. The said inert gas stream is stream of nitrogen, helium or other inert gases.

In accordance with the process of the present invention for preparing ethyl benzene by alkylation of benzene with ethylene, the preferred reaction operation conditions include a reaction temperature within the range of 320 to 450° C., a reaction pressure within the range of 0.1 to 2.0 MPa, an ethylene weight hourly space velocity within the range of 0.4 to 5 hr$^{-1}$, the mole ratio of benzene to ethylene within the range of 2 to 30, and a concentration of ethylene in ethylene raw material within the range of 5 to 100 vol %, namely ethylene raw material may be pure ethylene or dilute ethylene such as catalytic cracking dry gas or ethylene diluted by other gases. There is no special requirement for ethylene raw material except that its $H_2S$ content shall not exceed 6000 mg/m$^3$, $CO_2$ content not exceed 4 vol %, the content of alkene of $C_3$ to $C_4$ not exceed 2 vol % and water content not exceed 2000 ppm.

The process for preparing ethyl benzene by alkylation of benzene with ethylene provided by this invention may be used in alkylation of benzene with ethylene raw material in which ethylene concentration ranges from 5 to 100 vol %. Increasing the reaction pressure and the mole ratio of benzene to ethylene is advantageous to the reaction. However, if the pressure or the mole ratio is too high, it will increase energy consumption and the quantity of substances to be treated when separating the product, therefore they should not be too high. When pure ethylene is used as ethylene raw material, the preferred reaction conditions include a reaction temperature within the range of 360 to 450° C., a reaction pressure within the range of 0.2 to 2.0 MPa, an ethylene weight hourly space velocity within the range of 0.4 to 2.5 hr$^{-1}$, a mole ratio of benzene to ethylene within the range of 8 to 30. When dilute ethylene is used as ethylene raw material, the preferred reaction conditions include a reaction temperature within the range of 350 to 450° C., a reaction pressure within the range of 0.5 to 2.0 MPa, an ethylene weight hourly space velocity within the range of 0.4 to 3.0 hr$^{-1}$, a mole ratio of benzene to ethylene within the range of 4 to 10. To sum up, in the process for preparing ethyl benzene provided by this invention, the reaction conditions include most preferably a reaction temperature within the range of 350 to 450° C., a reaction pressure within the range of 0.2 to 2.0 MPa, an ethylene weight hourly space velocity within the range of 0.4 to 3.0 $hr^{-1}$, and a mole ratio of benzene to ethylene with the range of 4 to 30.

The process for preparing ethyl benzene provided by this invention has no special requirement for the reaction equipment, which may be a conventional reaction equipment such as fixed-bed reactor.

The catalyst provided by the present invention has higher activity, selectivity, as well as much higher stability in alkylation process than that of the prior art. For example, when the alkylation reaction of benzene with ethylene using pure ethylene having concentration of 99.4 vol % as raw material is performed over the catalyst of this invention under the conditions including a pressure of 1.0 MPa, an ethylene weight hourly space velocity of 0.8 $hr^{-1}$, a mole ratio of benzene to ethylene of 12, at an initiate reaction temperature of 350° C. and a final temperature of 450° C. by elevating the reaction temperature gradually, the system can run continuously for 120 days, wherein maintaining the ethylene conversion between 99 and 100 wt % for 102 days and between 98 and 99 wt % for 18 days; during the whole operation the ethyl benzene selectivity is more than 90% and alkylation selectivity is more than 99%. Under the same conditions with a ZSM-5 zeolite catalyst of the prior art, the operation can only run for 67 days, in which ethylene conversion is between 99 to 100 wt % for 50 days and between 98 to 99 wt % for 17 days; during the whole operation period the ethyl benzene selectivity is higher than 88% and alkylation selectivity is higher than 99%. When benzene and dilute ethylene, which is a catalytic cracking dry gas containing 19.5 vol % of ethylene and 0.8 vol % of propylene are used as raw materials to perform alkylation reaction with the catalyst provided by this invention under conditions including a pressure of 0.9 MPa, an ethylene weight hourly space velocity of 0.8 $hr^{-1}$, a mole ratio of benzene to ethylene of 10 and at an adiabatic reactor inlet initiate temperature of 350° C. and an outlet final temperature of 450° C., the system can run continuously for 75 days to maintain the ethylene conversion between 99 and 100 wt %, propylene conversion higher than 85 wt % and alkylation selectivity (as total amount of ethyl benzene and diethyl benzene produced) about 99%, while increasing gradually the reaction temperature to keep ethylene conversion above 98 wt %, the system can run continuously for 95 days to maintain the alkylation selectivity of 99%. Under the same conditions with a lanthanum ZSM-5 zeolite catalyst of the art the system can only run for 42 days; while increasing gradually the reaction temperature to control ethylene conversion above 98 wt %, the system can run continuously only for 53 days to maintain the alkylation selectivity of 99%. Besides, the catalyst provided by this invention has higher stability against acidic hydrothermal condition and this may be one of the reasons for the above advantages of the present invention.

The process for preparing ethyl benzene by alkylation of benzene with ethylene provided by this invention has the advantages of high ethylene conversion and good selectivity and is suitable for the alkylation process of ethylene raw material containing from 5 to 100 wt % of ethylene. For example, when the alkylation reaction of benzene with pure ethylene having a concentration of 99.4 vol % is performed over the catalyst of this invention under the conditions including a reaction temperature ranging from 360 to 450° C., a reaction pressure ranging from 0.4 to 2.0 MPa, an ethylene weight hourly space velocity ranging from 0.5 to 2.5 $hr^{-1}$ and a mole ratio of benzene to ethylene greater than 8, the ethylene conversion is higher than 99 wt %, the ethyl benzene selectivity is between 85.2 and 96.3% and alkylation selectivity (calculated as the total amount of ethyl benzene and diethyl benzene produced) is approximately 100%; while the alkylation reaction of benzene with dilute ethylene using a catalytic cracking dry gas containing 19.5 vol % of ethylene as raw material is performed over the catalyst provided by this invention under the conditions including a reaction temperature ranging from 350 to 450° C., a reaction pressure ranging from 0.5 to 2.0 MPa, an ethylene weight hourly space velocity ranging from 0.4 to 3.0 $hr^{-1}$ and a mole ratio of benzene to ethylene ranging from 4 to 10, the ethylene conversion is approximately 100 wt %. In addition, the process for preparing ethyl benzene by alkylation of benzene with ethylene provided by this invention has the advantages of no special requirement for ethylene raw material and allowing higher impurity contents and unpre-refined raw material, for example, in the ethylene raw material the contents of $H_2S$, $CO_2$, alkene of $C_3$ to $C_4$ and water may be up to 6000 $mg/m^3$, 4 vol %, 2 vol % and 2000 ppm respectively.

The present invention is described in further detail in connection with the following examples, it must be understood that the examples are for purposes of illustration and shall not be construed as limiting the scope of this invention.

EXAMPLE 1

This example is to prepare a catalyst of the present invention.

3000 ml of sodium silicate (containing 180 g/l $SiO_2$, 60 g/l $Na_2O$) was mixed completely with 1900 ml of deionized water and 250 g of hexanediamine having a content of 98% to form an operation liquid I.

51 g of $AlCl_3 \cdot 6H_2O$ having a content of 97% was mixed completely with 400 ml of $H_2SO_4$ having a concentration of 4M, 35 g of $LaCl_3 \cdot 6H_2O$ having a content of 99% and 2100 ml of deionized water to form an operation liquid II.

Under vigorously stirring the operation liquids I and II were mixed to form gel, stirred continuously for another 30 minutes, then the rate of stirring was lowered to about 100 rpm; heated to 175° C., kept at this temperature, and crystallized for 72 hours under stirring.

After the crystallization was completed, the mixture was cooled rapidly to the room temperature and filtered, the crystalline obtained was washed with deionized water until the pH of the wash filtrate was within the range of 8 to 9, filtered, dried at 110±10° C. for 10 hours to give La-ZSM-5/ZSM-11 co-crystalline zeolite.

This zeolite is characterized by X-ray diffraction pattern comprising the X-ray diffraction lines and assigned relative intensities shown in Table 1, and has a ratio of silica to alumina of 53, La content of 2.50 wt %, a weight ratio of ZSM-5 crystalline structure portion to ZSM-11 crystalline structure portion of 30:70, unit cell parameters for ZSM-5 crystalline structure as follows:

a=2.0118 nm, b=1.9970 nm, c=1.3426 nm, unit cell volume V=5.393 $nm^3$, unit cell parameters for ZSM-11 crystalline structure as follows:

a=b=1.9989 nm, c=1.3420 nm, unit cell volume V=5.362 $nm^3$, and adsorption capacities of 10.2 wt %, 4.0 wt % and 6.0 wt % respectively for n-hexane, cyclohexane and water. The unit cell parameters of zeolites and the weight ratio of ZSM-5 crystalline structure portion to ZSM-11 crystalline structure portion were calculated from the results of X-ray diffraction pattern. The adsorption capacities for n-hexane and cyclohexane were determined at 25° C. and an adsorbate partial pressure of 20 mmHg, and the adsorption capacity for water was determined at 25° C. and an adsorbate partial pressure of 12 mmHg. The contents of lanthanum and rare earth elements were determined by means of chemical analysis.

The X-ray diffraction lines shown in Table 1 were determined by standard techniques. The radiation was the K-alpha doublet of copper, and a scintillation counter and a nickel filter were used. In the table the interplanar spacing (d) corresponding to each diffraction peak was calculated from the Bragg equation and the position of the peak read from the spectrometer chart as a function of 2θ, where θ is the Bragg angle. The relative intensity (100 I/I$_0$) shown in the table is 100 times the ratio of each recorded diffraction peak height (namly diffraction intensity) I to the peak height of the highest recorded peak (the strongest diffraction intensity) I$_0$. In Table 1, the relative intensities are given in terms of the symbols: VS (very strong) which represents the value of relative intensity ranging from 100 to 60, S (strong) which represents the value of relative intensity ranging from 60 to 40, M (medium) which represents the value of relative intensity ranging from 40 to 20 and W (weak) which represents the value of relative intensity below 20.

La-ZSM-5/ZSM-11 co-crystalline zeolite synthesized above was mixed with Al$_2$O$_3$.3H$_2$O such that the weight ratio of zeolite to Al$_2$O$_3$ is 65:35 (in dry solid basis). To this mixture were added small quantities of nitric acid having a concentration of 20% and sesbania powder. The resulted mixture was then kneaded and extruded into particles having a size of φ2×2~4 mm, which were dried at 120° C. for 24 hours and calcined in air at 540° C. for 6 hours. Then ion-exchange with a mixture of 0.8 N NH$_4$NO$_3$ solution and 0.1 N NH$_4$OH at 90° C. at a liquid-to-solid ratio of 10 was carried out. The solid was filtered out, washed until the wash filtrate had no NO$_3$, dried at 110° C. for 24 hours and calcined in air at 540° C. for 4 hours to give product A' having sodium oxide content less than 0.05 wt %. This product was treated in 100% steam at 550° C. for 4 hours to give catalyst A. In the catalyst A the content of rare earth element was 1.60 wt %. The amount of the acid sites having desorption temperature between 320 and 450° C. (which are acid sites of medium strength) was 66% of the total amount of acid sites, as determined by the TPD method.

EXAMPLE 2

This example is to prepare a catalyst of the present invention.

580 ml of sodium silicate (as used in Example 1) was mixed completely with 420 ml of deionized water and 58 g of hexanediamine having a content of 98% to form an operation liquid I.

49.5 g of aqueous AlPO$_4$ gel containing 5.4 wt % of Al$_2$O$_3$ was mixed thoroughly with 74 ml of H$_2$SO$_4$ having a concentration of 4M, 13.4 g of RECl$_3$.6H$_2$O having a content of 98% (in which the weight ratio of La$_2$O$_3$ to Ce$_2$O$_3$ is 0.6) and 351 ml of deionized water to form an operation liquid II.

Under vigorously stirring the operation liquids I and II were mixed to form gel, stirred continuously for another 5 minutes, then the rate of stirring was lowered to about 100 rpm; heated to 110° C., crystallized for 16 hours wider stirring, then heated to 180° C. and crystallized continuously for 38 hours under stirring.

After crystallization completed the mixture was cooled rapidly to room temperature and filtered, the crystalline was washed with deionized water until the pH of the wash filtrate was within the range of 8 to 9, filtered, dried at 110±10° C. for 10 hours to give RE-ZSM-5/ZSM-11 co-crystalline zeolite.

This zeolite is characterized by X-ray diffraction pattern comprising the X-ray diffraction lines and assigned relative intensities shown in table 1, and had a silica-to-alumina ratio of 35, RE content of 4.50 wt %, a weight ratio of ZSM-5 crystalline structure portion to ZSM-11 crystalline structure portion of 40:60, and adsorption capacities of 9.8 wt %, 3.2 wt % and 6.5 wt % respectively for n-hexane, cyclohexane and water. All results were determined by similar methods as that in Example 1.

Catalyst B was prepared from RE-ZSM-5/ZSM-11 co-crystalline zeolite synthesized above according to the method described in Example 1. In the catalyst B the content of rare earth element was 2.90 wt %, and the amount of the medium strength acid sites was 57 % of the total amount of acid sites.

EXAMPLE 3

This example is to prepare a catalyst of the present invention.

400 ml of sodium silicate (containing 223 g/l SiO$_2$, 70.4 g/l Na$_2$O ) was mixed completely with 326 ml of deionized water, 13 g of ethylenediamine and 21 g of hexanediamine (both diamines having contents of 98%) to form an operation liquid I.

11.5 g of Al$_2$(SO$_4$)$_3$.18H$_2$O having content of 99% was mixed completely with 67 ml of H$_2$SO$_4$ having a concentration of 4M, 11 g of LaCl$_3$.6H$_2$O having a content of 99% and 370 ml of deionized water to form an operation liquid II.

Under vigorously stirring the operation liquids I and II were mixed to form gel, stirred continuously for another 5 minutes, then the rate of stirring was lowered to about 100 rpm, heated to 170° C., kept at this temperature and crystallized for 70 hours under stirring.

After crystallization completed the mixture was cooled rapidly to room temperature and filtered, the crystalline was washed with deionized water until the pH of the wash filtrate was within the range of 8 to 9, filtered, dried at 110±10° C. for 10 hours to give La-ZSM-5/ZSM-11 co-crystalline zeolite.

This zeolite is characterized by X-ray diffraction pattern comprising the X-ray diffraction lines and assigned relative intensities shown in Table 1, and had a silica-to-alumina ratio of 60, La content of 5.20 wt %, a weight ratio of ZSM-5 crystalline structure portion to ZSM-11 crystalline structure portion of 60:40, and adsorption capacities of 11.7 wt %, 3.0 wt % and 5.3 wt % respectively for n-hexane, cyclohexane and water.

Catalyst C was prepared from La-ZSM-5/ZSM-11 co-crystalline zeolite synthesized above according to the method described in Example 1. In the catalyst C the content of rare earth element was 3.32 wt %. The amount of the medium strength acid sites was 62% of the total amount of acid sites.

Comparative Example 1

This comparative example is to prepare a comparative catalyst.

1910 ml of sodium silicate solution (containing 193.21 mg $SiO_2$/ml, 62.58 mg $Na_2O$/ml) was mixed completely with 1310 ml of deionized water and 200 g of tetrapropylammonium bromide.

46 g of $Al_2(SO_4)_3 \cdot 18H_2O$ having a content of 99 wt % was mixed completely with 320 ml of $H_2SO_4$ having a concentration of 4M, and 1320 ml of deionized water.

Under vigorously stirring the two liquids obtained above were mixed to form gel. The gel was moved into a 10-liter stainless steel pressure vessel and crystallized at 175° C. for 72 hours. The product was cooled rapidly, washed with pure water several times until the pH of the wash filtrate was within the range of 8 to 9. The filter cake was dried at 120° C. for 10 hours to give Na-ZSM-5 zeolite. This zeolite had a silica-to-alumina mole ratio of 48, and adsorption capacities of 10.5 wt %, 5.2 wt % and 5.4 wt % respectively for n-hexane, cyclohexane and water.

Comparative catalyst D was prepared from Na-ZSM-5 zeolite synthesized above according to the method described in Example 1. In the comparative catalyst D the content of sodium oxide was less than 0.05 wt %.

Comparative Example 2

This comparative example is to prepare a comparative catalyst.

100 g of the catalyst prepared in Comparative Example 1 and not treated under hydrothermal condition was impregnated in 130 ml of $La(NO_3)_3$ aqueous solution having La content of 12.8 mg/ml at room temperature for 24 hours, dried in an oven at 120° C. for 15 hours, calcined at 540° C. for 3 hours, and treated in 100% steam at 550±10° C. for 4 hours to give comparative catalyst E containing 1.65 wt % of lanthanum element.

EXAMPLE 4

This example is to illustrate the stability of the catalyst provided by this invention against acidic hydrothermal condition.

The difference between acidities for catalysts before and after hydrothermal treatment (A' and A prepared in example 1) was determined by means of temperature programmed desorption (TPD) of ammonia. The analysis conditions included helium used as carrier gas with a flow rate of 20 ml/min, pre-activating the sample in an adsorption tube at 600° C. for 45 minutes, cooling to 150° C., introducing ammonia to perform adsorption at constant temperature, purging with carrier gas for 30 minutes at constant temperature after adsorption saturated, and then desorbing ammonia while increasing the temperature at a rate of 20° C./min. The signals of ammonia desorption at temperatures between 200 and 600° C. were recorded by chromatography, the total amount of acid sites of the sample was calculated by area normalization, and the results are listed in Table 2.

Comparative Example 3~4

These comparative examples are to illustrate the higher acidic hydrothermal stability of the catalyst provided by this invention than that of the prior art.

The catalysts prepared in comparative examples 1 and 2 were treated hydrothermally and their amounts of acid sites were determined according to the method in Example 4. The results are shown in Table 2.

As can be seen from Table 2, the catalyst provided by the present invention has higher acidic hydrothermal stability than that of the prior art. This is highly significant in industrial practice for the catalytic processes involving hydrothermal treatment such as regeneration of catalysts. It also means that the catalysts of the present invention has not only good activity, stability and longer single operation cycle in the reaction process, but also has good regeneration property and longer life.

TABLE 2

| Sample | Relative total acidity | |
|---|---|---|
| | before hydrothermal treatment | after hydrothermal treatment |
| Catalyst from Example 1 | 100 | 91 |
| Catalyst from Comparative Example 1 | 100 | 79 |
| Catalyst from Comparative Example 2 | 100 | 85 |

EXAMPLE 5

This example is to illustrate the activity, selectivity and stability of the catalyst provided by this invention for the alkylation process.

A continuous flow fixed-bed reactor having an inner volume of 25 ml was charged with 10 ml of catalyst C prepared in Example 3 to perform alkylation of benzene with ethylene. The reaction conditions included ethylene having the purity of 99.4 vol % and benzene having the purity of 99.0 wt % as raw materials, a reaction pressure of 1.0 MPa, an ethylene weight hourly space velocity of 0.8 $hr^{-1}$, a benzene-to-ethylene mole ratio of 12, an initial reaction temperature of 350° C., a final temperature of 450° C. and the reaction temperature being increased gradually to maintain the ethylene conversion. The system was run continuously for 120 days, in which the ethylene conversion was kept between 99 and 100 wt % for 102 days and between 98 and 99 wt % for 18 days and during the whole operation process the selectivity of ethyl benzene among the products formed was more than 90% and alkylation selectivity (as total amount of ethyl benzene and diethyl benzene produced) was higher than 99%.

Comparative Example 5

This comparative example is to illustrate that in the alkylation process the catalyst provided by this invention has higher activity and selectivity, and more particularly much higher stability than that of the prior art.

An alkylation of benzene with ethylene was performed in the same reactor, under the same reaction conditions and with the same raw materials, as used in Example 5, but catalyst D prepared in comparative example 1 was used. The system was run continuously for 67 days while increasing gradually the reaction temperature to maintain ethylene conversion, in which the ethylene conversion was between 99 and 100 wt % for 50 days and between 98 and 99 wt % for 17 days, and during the whole operation process the selectivity of ethyl benzene among the products formed was higher than 88% and alkylation selectivity was higher than 99%.

EXAMPLE 6

This example is to illustrate the activity, selectivity and stability of the catalyst provided by this invention.

An adiabatic continuous flow fixed-bed reactor having an inner volume of 200 ml was charged with 100 ml of catalyst A prepared in Example 1 to perform alkylation of benzene with dilute ethylene. The benzene raw material had a purity of 99.0 wt %. The dilute ethylene raw material was catalytic cracking dry gas containing 33.0 vol % methane, 19.5 vol % ethylene, 16.0 vol % ethane, 14.0 vol % hydrogen, 10.5 vol % nitrogen, 4.0 vol % carbon dioxide, 1.5 vol % carbon monoxide, 0.8 vol % propylene, 0.2 vol % propane, 0.5 vol % oxygen, 3500 mg/m$^3$ hydrogen sulfide and 1500 ppm water. The reaction conditions included a reaction pressure of 0.9 MPa, an ethylene weight hourly space velocity of 0.8 hr$^{-1}$, a benzene-to-ethylene mole ratio of 10, a reactor inlet initial temperature of 350° C. and an outlet final temperature of 450° C. The system could run continuously for 75 days while maintaining ethylene conversion between 99 and 100 wt %, propylene conversion over 85 wt % and alkylation selectivity about 99%. By increasing reaction temperature gradually to control ethylene conversion over 98%, the system could run continuously for 95 days while maintaining alkylation selectivity about 99%.

Comparative Example 6

This comparative example is to further illustrate that the catalyst provided by this invention has higher stability in alkylation process than that of the prior art.

Alkylation of benzene with ethylene was performed in the same reactor, under the same reaction conditions and with the same raw materials, as used in Example 6. But the catalyst B prepared in Comparative Example 2 was used. The system could run continuously for 42 days while maintaining ethylene conversion between 99 and 100 wt % and propylene conversion over 85%. By increasing reaction temperature gradually to control ethylene conversion over 98 wt %, the system could run continuously for 53 days while maintaining alkylation selectivity about 99%.

EXAMPLE 7~22

These examples are to illustrate the preferred reaction operation conditions in the process provided by this invention for preparing ethyl benzene by alkylation of benzene with pure ethylene as ethylene raw material.

A continuous flow fixed-bed reactor having an inner volume of 25 ml was charged with 10 ml catalyst C prepared in Example 3 to perform alkylation of benzene with ethylene, wherein benzene raw material had a purity of 99.0 vol % and ethylene raw material had a purity of 99.4 wt %. The results obtained under various reaction conditions are listed in Table 3.

The process for preparing ethyl benzene by alkylation of benzene with ethylene provided by this invention may be performed under conventional reaction conditions in the art. The results shown in Table 3 illustrate that with pure ethylene as ethylene raw material the preferred reaction conditions include a reaction temperature ranging from 360 to 450° C., a reaction pressure ranging from 0.2 to 2.0 MPa, an ethylene weight hourly space velocity ranging from 0.4 to 2.5 hr$^{-1}$, a benzene-to-ethylene mole ratio ranging from 8 to 30. The results from Table 3 also illustrate that the process of this invention has higher ethylene conversion, ethyl benzene selectivity and alkylation selectivity than that of the prior art.

TABLE 3

The alkylation reaction conditions and results

| Example No. | Reaction Temperature ° C. | Reaction Pressure MPa | Ethylene WHSV hr$^{-1}$ | Benzene/ ethylene mole ratio | Ethylene conversion wt % | Ethyl Benzene selectivity % | Alkylation selectivity % |
|---|---|---|---|---|---|---|---|
| 7 | 375 | 1.0 | 1.00 | 8.00 | 99.8 | 88.5 | 99.9 |
| 8 | 400 | 1.0 | 1.00 | 8.01 | 100.0 | 90.1 | 99.9 |
| 9 | 425 | 1.0 | 1.00 | 8.45 | 100.0 | 92.3 | 99.8 |
| 10 | 450 | 1.0 | 1.00 | 8.30 | 99.0 | 94.7 | 99.4 |
| 11 | 380 | 0.5 | 0.96 | 10.20 | 99.8 | 88.7 | 99.9 |
| 12 | 381 | 1.0 | 1.00 | 9.88 | 99.9 | 90.3 | 99.8 |
| 13 | 380 | 1.5 | 1.11 | 10.16 | 100.0 | 91.8 | 99.9 |
| 14 | 378 | 2.0 | 1.15 | 9.80 | 100.0 | 90.1 | 99.7 |
| 15 | 400 | 0.80 | 0.41 | 27.01 | 100.0 | 94.4 | 100.0 |
| 16 | 399 | 0.80 | 0.70 | 15.25 | 100.0 | 93.1 | 100.0 |
| 17 | 399 | 0.80 | 1.10 | 9.57 | 99.9 | 96.3 | 99.9 |
| 18 | 400 | 0.80 | 2.34 | 3.65 | 98.5 | 85.2 | 98.5 |
| 19 | 396 | 1.0 | 0.48 | 10.00 | 100.0 | 90.6 | 99.5 |
| 20 | 400 | 1.0 | 2.06 | 8.54 | 99.5 | 86.7 | 99.9 |
| 21 | 400 | 1.0 | 2.50 | 10.00 | 99.1 | 85.4 | 99.9 |
| 22 | 400 | 1.0 | 3.00 | 9.66 | 95.2 | 80.6 | 99.9 |

EXAMPLE 23~36

These examples are used to illustrate the preferred reaction operation conditions in the process provided by this invention for preparing ethyl benzene by alkylation of benzene with dilute ethylene as ethylene raw material.

An adiabatic continuous flow fixed-bed reactor having an inner volume of 200 ml was charged with 100 ml of catalyst A prepared in Example 1 to perform alkylation of benzene with dilute ethylene, wherein benzene raw material had a purity of 99.0 wt %, dilute ethylene raw material was catalytic cracking dry gas containing 33.0 vol % methane, 19.5 vol % ethylene, 16.0 vol % ethane, 14.0 vol % hydrogen, 10.5 vol % nitrogen, 4.0 vol % carbon dioxide, 1.5 vol % carbon monoxide, 0.8 vol % propylene, 0.2 vol % propane, 0.5 vol % oxygen, 3500 mg/m$^3$ hydrogen sulfide and 1500 ppm water. The results obtained under various reaction conditions listed in Table 4.

The results shown in Table 4 illustrate that with dilute ethylene as ethylene raw material preferred reaction conditions for the process of the present invention include a reaction temperature ranging from 350 to 450° C., a reaction pressure ranging from 0.5 to 2.0 MPa, an ethylene weight hourly space velocity ranging from 0.4 to 3.0 hr$^{-1}$, a benzene-to-ethylene mole ratio ranging from 4 to 10. The results from Table 4 also show that the process provided by this invention for preparing ethyl benzene by alkylation of benzene with ethylene has higher ethylene conversion, ethyl benzene selectivity and alkylation selectivity than that of the prior art.

EXAMPLE 37~38

These examples are used to illustrate that the process provided by this invention for preparing ethyl benzene by alkylation of benzene with ethylene is suitable for different raw materials.

An alkylation of benzene with ethylene was performed in the same reactor, under the same reaction conditions, with the same raw materials, over the same catalyst as used in Examples 23 ~36 except that the concentration of ethylene was 7.2 vol % and 28.5 vol %, respectively, in the catalytic cracking dry gases as dilute ethylene raw materials. The reaction conditions and results are also listed in Table 4.

TABLE 4

The alkylation reaction conditions and results

| Example No. | Reaction Temperature ° C. | Reaction Pressure MPa | Ethylene WHSV hr$^{-1}$ | Benzene/ Ethylene mole ratio | Ethylene Conversion wt % | Ethyl Benzene Selectivity % | Alkylation Selectivity % |
|---|---|---|---|---|---|---|---|
| 23 | 350 | 0.80 | 1.00 | 5.5 | 98.2 | 88.8 | 100.0 |
| 24 | 375 | 0.80 | 1.00 | 5.0 | 99.1 | 90.8 | 99.9 |
| 25 | 400 | 0.80 | 1.00 | 5.8 | 100 | 91.4 | 99.9 |
| 26 | 425 | 0.80 | 1.00 | 5.0 | 99.5 | 92.0 | 99.8 |
| 27 | 450 | 0.80 | 1.00 | 5.4 | 98.0 | 92.5 | 98.7 |
| 28 | 385 | 0.50 | 1.50 | 4.5 | 96.6 | 85.7 | 99.8 |
| 29 | 385 | 1.00 | 1.50 | 4.0 | 98.5 | 89.1 | 99.9 |
| 30 | 385 | 1.50 | 1.80 | 4.7 | 99.0 | 90.8 | 99.8 |
| 31 | 385 | 2.00 | 2.20 | 5.0 | 99.2 | 91.4 | 99.8 |
| 32 | 380 | 0.80 | 1.80 | 8.0 | 99.1 | 88.3 | 98.5 |
| 33 | 380 | 0.80 | 1.20 | 5.0 | 99.0 | 89.7 | 99.8 |
| 34 | 380 | 0.80 | 1.00 | 7.0 | 99.5 | 90.6 | 99.9 |
| 35 | 380 | 0.80 | 0.80 | 10.00 | 100.0 | 92.2 | 100.0 |
| 36 | 400 | 0.80 | 2.50 | 7.0 | 99.0 | 89.8 | 99.9 |
| 37 | 400* | 0.80 | 0.80 | 7.0 | 99.0 | 88.1 | 99.8 |
| 38 | 400** | 0.80 | 1.00 | 7.0 | 99.2 | 90.3 | 99.7 |

*In dilute ethylene raw material, the concentration of ethylene was 7.2 vol %.
**In dilute ethylene raw material, the concentration of ethylene was 28.5 vol %

What is claimed is:

1. An alkylation catalyst comprising from 50 to 70 wt %, based on the weight of the catalyst, of a hydrogen type ZSM-5/ZSM-11 co-crystalline zeolite containing a rare earth element, the balance being a porous inorganic oxide matrix material, wherein the zeolite has a weight ratio of ZSM-5 crystalline portion to ZSM-11 crystalline portion within the range of 0.25 to 2.5, and in an originally synthesized anhydrous state a chemical composition formula in mole ratios of oxides as follows:

$$XNa_2O \cdot YRE_2O_3 \cdot Al_2O_3 \cdot ZSiO_2$$

wherein X is within the range of 0.1 to 1.0, Y is within the range of 0.1 to 1.0 and Z is within the range of 20 to 100, the zeolite having an X-ray diffraction pattern comprising X-ray diffraction lines and respective relative intensities as shown in the following table:

| d(Å) | 100 I/I$_o$ |
|---|---|
| 11.2 ± 0.2 | M |
| 10.1 ± 0.2 | M |
| 6.05 ± 0.14 | W |

-continued

| d(Å) | 100 I/I$_o$ |
|---|---|
| 4.40 ± 0.08 | W |
| 3.86 ± 0.07 | VS |
| 3.72 ± 0.07 | S |
| 3.65 ± 0.07 | W–M |
| 2.01 ± 0.02 | W |

VS = very strong (100–60); S = (60–40); M = medium (40–20); W = weak (<20).

2. The alkylation catalyst according to claim 1, wherein the porous inorganic oxide matrix material is alumina.

3. The catalyst according to claim 1, wherein the rare earth element is lanthanum or a mixture of rare earth elements, and wherein the rare earth element is present on an elemental basis in the catalyst in an amount ranging from 0.5 to 5 wt %, based on the weight of the catalyst.

4. The catalyst according to claim 3, wherein the content of sodium oxide in the catalyst is less than 0.05 wt %, based on the weight of the catalyst.

5. The process for preparing ethyl benzene by alkylation of benzene with ethylene, the process comprising contacting benzene and ethylene with the catalyst according to claim 1, under conditions at which the alkylation reaction can be performed, and separating ethyl benzene from side products and unreacted reactants.

6. The process according to claim 5, wherein the porous inorganic oxide matrix material of the catalyst is alumina.

7. The process according to claim 5, wherein the conditions comprise a reaction temperature within the range of 320 to 450° C., a reaction pressure within the range of 0.1 to 2.0 MPa, an ethylene weight hourly space velocity within the range of 0.4 to 5.0 hr$^{-1}$, and a molar ratio of benzene to ethylene within the range of 2 to 30.

8. The process according to claim 7, wherein the reaction conditions comprise a reaction temperature within the range of 350 to 450° C., a reaction pressure in the range of 0.2 to 2.0 MPa, an ethylene weight hourly space velocity in the range of 0.4 to 3.0 hr$^{-1}$, and a molar ratio of benzene to ethylene within the range of 4 to 30.

* * * * *